US00PP10011P

United States Patent [19]

Roberson

[11] Patent Number: Plant 10,011

[45] Date of Patent: Aug. 26, 1997

[54] LANTANA PLANT NAME 'ROBPATHON'

[76] Inventor: Robert J. Roberson, 31706 E. Pink Hill Rd., Grain Valley, Jackson County, Mo. 64029

[21] Appl. No.: 671,579

[22] Filed: Jun. 28, 1996

[51] Int. Cl.[6] ..... A01H 5/00

[52] U.S. Cl. ..... Plt./54.1

[58] Field of Search ..... Plt./54.1, 68.1

*Primary Examiner*—James R. Feyrer

*Attorney, Agent, or Firm*—Rothwell, Figg, Ernst & Kurz, PC

[57] ABSTRACT

A new cultivar of Lantana is provided, characterized particularly as to novelty by the new color break of cantaloupe-peach in recumbent, weeping, forms of Lantanas, with vigorous and rapid ground cover tendency, reduced tendency to set seed and its continuous blooming.

2 Drawing Sheets

SUMMARY OF THE INVENTION

This invention relates to a new and distinct *Lantana camara* cultivar which is outstanding because of its new color for prostrate Lantanas, its rapid, prostrate growth habit with tendency for self-branching, its long-term blooming performance, its reduced tendency to set seed, its highly aromatic medium green foliage; and was primarily selected for these characteristics. This selection was made from a specially designed Lantana hybridizing program with said hybrid cultivars being planted and grown in Grain Valley, Mo.

Origin and Asexual Reproduction

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America and are woody ornamentals which are not winter hardy North of USDA horticulture Zone 9. The roughish leaves range from yellow-green to green to blue-green and the two basic growth forms are mounding and trailing (weeping). Bloom color usually includes yellow, white, cream, pink, or orange.

The cultivar of *Lantana camara* 'Robpathon' may further be described as having a number of distinctive characteristics which are enumerated in the succeeding specific description but broadly stated as comprising a new color (cantaloupe-peach) among weeping Lantanas, a prostrate weeping form with rapid growth and strong tendency to self branching (which gives a dense low carpet effect), a continuous multi-colored bloom display {which transitions from yellow-gold (PMS #114) through tones of cantaloupe peach (PMS #142 and #162), and matures as a cantaloupe-peach (PMS #169)}, dense, aromatic green (PMS #371) leaves, and a reduced tendency to set seed, allowing more continuous blooming. The continuous color display begins blooming at 6–7 weeks after cuttings are made, or 4 weeks after potting. I have chosen to identify this new cultivar as *Lantana Camara* 'Robpathon'. It is possible that other identification will be adopted in the trade, but the name selected will serve for the purposes thereof.

BRIEF DESCRIPTION OF THE DRAWING

The accompanying photographs show as nearly true as it is reasonably possible to make the same, in color illustrations of this character, typical flowers of the new variety. The photographic drawings illustrate the flower form, the distinctive color transitions of the florets, and the dense, prostrate growth habit.

DETAILED DESCRIPTION

Figure 1:
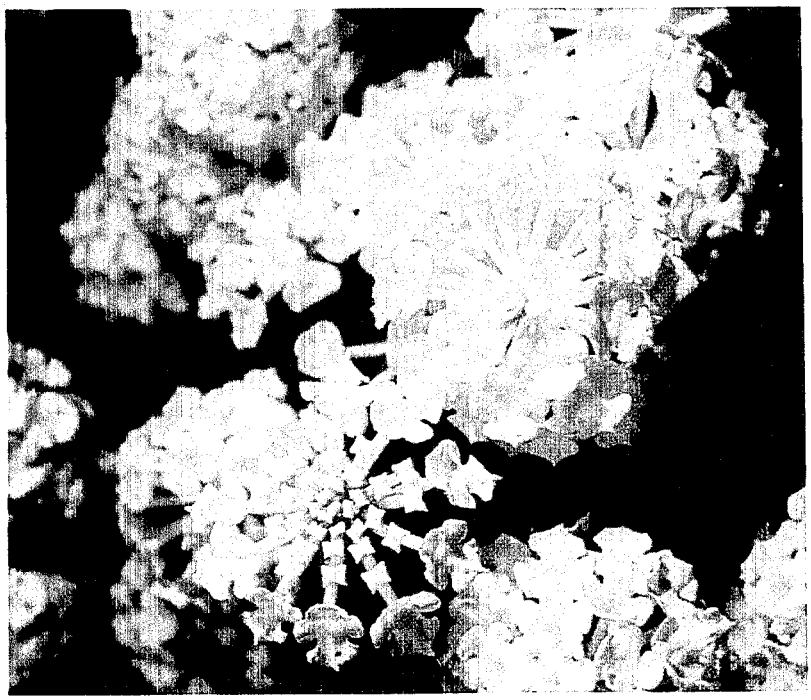
FIG. 1 illustrates the bloom cluster with varying maturity of the florets (to display the color range as well as possible).
Figure 2:
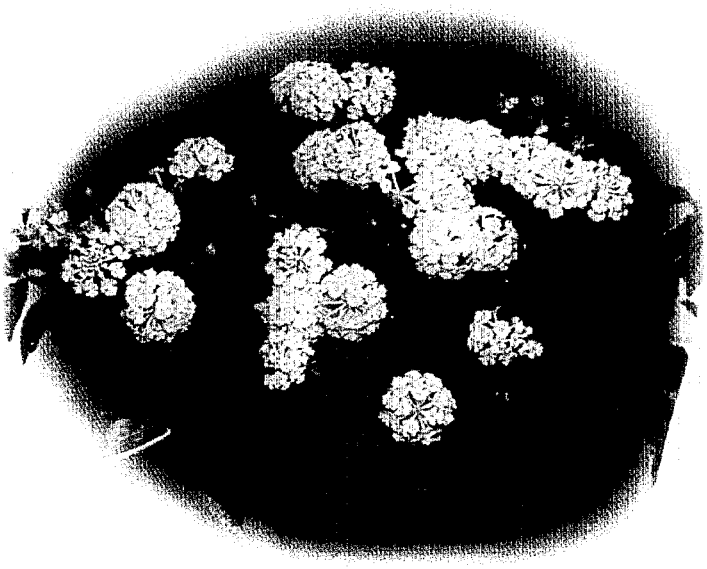
FIG. 2 illustrates the prostrate (weeping) growth habit of the mature plant, which adapts well in a hanging basket, as shown.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camara* 'Patriot™ Chiffon' (in controlled open pollination).

*Pollen parent.*—Unknown

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consists of: the Calyx (5 united petals) and the Corolla (5 united petals with narrow tube). The flowers are zygomorphic, hermaphroditic, and have 4 introse stamens which are didynamous.

The ovary is superior, the style is terminal, and the stigma is lobed. The ovary is 2 locular, but is divided into 4 loculi by a false septum in each loculus. The placentation is axile with 2 ovules per carpel.

The fruit classification is drupe and potentially contains 2 seeds. When fruit forms, it is green (PMS #363); then matures through a deep purple (PMS #533) to a near black (PMS#532).

*Inflorescence dimensions.*—Bloom cluster—1.7" in diameter. Single Floret—0.4". Pedicle length—1.6". Corolla tube—0.6".

*Inflorescence colors.*—Buds- Yellow (PMS#120). First opening- Yellow-gold (PMS#114). Transitions through- Pastel salmon tones of (PMS #142 and #162). Maturity- Pink-Cantaloupe (PMS #169). Tube- Cantaloupe (PMS #141).

Developmental pattern: First flowers develop in a circular pattern on the periphery of the inflorescence.

*Leaves and stems.*—Leaf shape: Ovate. Leaf margins: Serrate. Leaf tip and base: Acute. Leaf veins: Pinnate. Leaf surface: Rough due to bristly hairs. Leaf arrangement: Opposite. Leaf color: Medium Green (PMS #371) with very little change in color from immature to mature stage. Leaf size Length 2". Petiole: 0.4". Width: 1.2". Stem: Square in youth becoming round and woody with age.

*Roots.*—Highly branched and fibrous

*Flowering time.*—The color display begins blooming at 6–7 weeks after cuttings are made, or 4 weeks after potting, and continue until temperatures drop below 45 degrees Fahrenheit.

*Diseases.*—No unusual susceptibility to diseases noted to date.

*Insects.*—Typical of this plant genius, white flies can be attracted to Lantana. There are not other insect problems known at this time.

GENERAL OBSERVATIONS

*Lantana camara* 'Robpathon', is an excellent plant of choice for today's ornamental horticulture demand. The current trend toward smaller yards and balcony gardening lends itself to the type of uses for which Lantanas are ideal. This new cultivar, *Lantana camara* "Robpathon" is specifically appropriate for the following reasons:

A. "Robpathon" is a new color in weeping (prostrate form Lantanas, as all other prostrate forms currently available are either yellow, white or lavender. This particular color break offers to the gardener a new and popular color choice of peach-melon tones.

B. The rapid (15"–18" wide by 30" in diameter in one season) growth habit of this cultivar combined with it's weeping form and self-branching, make it ideal for today's demand for "instant" beauty and color in hanging baskets or ground covers for mass plantings.

C. This cultivar produces profusely blooming floret clusters which continue until temperatures drop below 45 degrees Fahrenheit.

D. This cultivar's reduced tendency to set seed is an asset in that it requires no "dead heading" to remove seeds; therefore it will continue to bloom all season without this type of care by the gardener.

COMPARISON TO KNOWN VARIETIES

Due to the unique color characteristics of this culture, there is no appropriate comparable plant available in the trade to make a comparison. There are other semi-weeping from Lantanas but none in this color category. This color characteristic is one of the positive features that aided in the selection of the plant.

I claim:

1. A new and distinct cultivar of *Lantana camara*, substantially as described herein, characterized particularly as to novelty by the new color break of cantaloupe-peach in recumbent, weeping, forms of Lantanas, with vigorous and rapid ground cover tendency, reduced tendency to set seed and its continuous blooming.

* * * * *